(12) United States Patent
Dietrich et al.

(10) Patent No.: US 8,349,572 B2
(45) Date of Patent: Jan. 8, 2013

(54) STABLE CELL LINES EXPRESSING HERG

(75) Inventors: Paul Shartzer Dietrich, Palo Alto, CA (US); Bruce Koch, Sunnyvale, CA (US); Heather Guthrie, Bloomfield, NJ (US); Ulrich Andreas Gubler, Glen Ridge, NJ (US)

(73) Assignee: Roche Palo Alto LLC, Palo Alto, CA (US)

( * ) Notice: Subject to any disclaimer, the term of this patent is extended or adjusted under 35 U.S.C. 154(b) by 65 days.

(21) Appl. No.: 12/820,358

(22) Filed: Jun. 22, 2010

(65) Prior Publication Data

US 2010/0261191 A1    Oct. 14, 2010

Related U.S. Application Data

(62) Division of application No. 11/637,511, filed on Dec. 11, 2006, now Pat. No. 7,776,590.

(60) Provisional application No. 60/841,965, filed on Sep. 1, 2006, provisional application No. 60/753,015, filed on Dec. 21, 2005.

(51) Int. Cl.
*C12Q 1/00* (2006.01)
(52) U.S. Cl. ............................................ 435/7.21; 435/4
(58) Field of Classification Search ........................ None
See application file for complete search history.

*Primary Examiner* — Daniel C Gamett
(74) *Attorney, Agent, or Firm* — Robert C. Hall

(57) ABSTRACT

A stable eukaryotic cell line that expresses hERG and exhibits a stable current under electrophysiological test conditions is provided.

5 Claims, No Drawings

STABLE CELL LINES EXPRESSING HERG

RELATED APPLICATIONS

This application is a divisional application of U.S. Ser. No. 11/637,511 filed Dec. 11, 2006, now U.S. Pat. No. 7,776,590 which claims priority from U.S. Ser. No. 60/753,015, filed Dec. 21, 2005, and U.S. Ser. No. 60/841,965, filed Sep. 1, 2006, all of which are incorporated herein by reference in full.

FIELD OF THE INVENTION

This invention relates generally to stable cell lines that express the voltage-gated hERG potassium channel, and methods of using said cells to test compounds for their ability to inhibit hERG current.

BACKGROUND OF THE INVENTION

Ion channels constitute a relatively small class of pharmaceutical targets, in part because ion channel screening assays have been difficult to automate and format for high throughput. However, recent advances in electrophysiology (P. B. Bennett et al., *Trends in Biotech* (2003) 21(12):563-69; C. Wood et al., *Drug Disc Today* (2004) 9(10):434-41) have rekindled interest in ion channels as targets for drug discovery. A number of ion channels have been linked to inherited diseases, leading to the study of ion channel modulators for the treatment and prevention of disease (D. Owen et al., *Drug Disc World* (2002) 48-61).

HERG is an ion channel of particular interest to the pharmaceutical industry, although as a safety/toxicology problem rather than a target for developing modulators (ICH S7B Guidance for Industry, October 2005; J. I. Vandenberg et al., *Trends Pharm Sci* (2001) 22(5):240-46). The voltage-gated hERG potassium channel contributes to the rapidly-activating delayed rectifier potassium current ($I_{Kr}$) of the cardiac action potential. Drug interaction with the hERG potassium channel has been implicated in electrocardiogram QT interval prolongation and the cardiac arrhythmia known as Torsades de Pointes ("TdP"; see C. E. Chiang and D. M. Roden, *J Am Coll Cardiol* (2000) 36(1):1-12.; D. M. Roden, *N Eng J Med* (2004) 350:1013-22.). TdP can be fatal, and the risk of inducing it has led to withdrawal and non-approval of pharmaceutical products.

High throughput screening of drug candidates to determine their possible effect on hERG has proven to be difficult, based in large part on the unavailability of a stable cell line that expresses hERG at sufficient surface concentrations, and is a suitable subject for high throughput ion flow measurement instruments.

SUMMARY OF THE INVENTION

We have now invented hERG expressing cell lines that reproducibly formed stable seals with large current amplitudes using standard and automated patch clamp set ups. The cell lines of the invention produce $IC_{50}$ values that are representative of those reported in the literature using non-high-throughput methods.

One aspect of the invention is a stable eukaryotic cell line that expresses hERG, and is capable of exhibiting a test current that varies by less than approximately 20% peak current amplitude under control conditions for over one hour.

Another aspect of the invention is a method for determining the propensity of a test compound to inhibit hERG conductance activity, by contacting a cell of the invention with said test compound, measuring a test current under electrophysiological conditions, and determining if the test current is lower in the presence of the test compound.

DETAILED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Antagonist" refers to a compound that diminishes or prevents the action of another compound or receptor site.

The term "drug candidate" refers to a compound or preparation which is to be tested for possible effect in the treatment of a disease state in an animal, regardless of whether said drug candidate has any known biological activity.

The term "homologous" as used herein refers to a protein that performs substantially the same function in another subject species and shares substantial sequence identity, to the extent that they are recognized in the art as being different versions of the same protein, differing primarily in the species in which they are found. Thus, for example, human ERG, mouse ERG, and rat ERG are all considered homologous to each other.

"Modulator" means a molecule that interacts with a target. The interactions include, but are not limited to, agonist, antagonist, and the like, as defined herein.

"Disease" and "Disease state" means any disease, condition, symptom, disorder or indication.

The term "cell line" refers to a clone of immortalized mammalian cells. A "stable" cell line is a cell line that exhibits substantially consistent characteristics over time (e.g., with each doubling). A stable cell line within the scope of this invention provides a substantial proportion of cells that are capable of providing a seal resistance of greater than about 50 MOhm, a current amplitude of greater than about 200 pA, and provide a current amplitude that does not vary by more than approximately 20% over one hour under control conditions.

The terms "progeny" and "descendents" as used herein refers to cells obtained by culturing or otherwise growing a cell of the invention.

The term "derivative" as used herein refers to a cell that is obtained by modifying, fusing, transfecting, transforming, or otherwise changing a cell of the invention. For example, derivatives can be created by transfecting a cell of the invention with a plasmid or virus, by fusing it to a hybridoma cell, and the like.

The term "electrophysiological measurements" or "patch clamp experiment" refer to an experimental procedure in which the voltage potential of part or all of a cell membrane (typically in an isolated cell) is maintained at a predetermined voltage, then subjected to one or more changes in voltage, during and/or after which the current passing through the membrane is measured. In the hERG measurement experiment used herein, a cell expressing hERG on its surface is first voltage clamped at a holding potential of −80 mV, leak subtraction was calculated from a 100 msec pulse to −40 mV, followed by 1000 msec at 20 mV (prepulse), and 500 msec at −40 mV (test pulse). hERG current was measured as the peak (beginning of the test pulse) at −40 mV after correction with leak current. Variations of this protocol can be applied. The hERG current inhibition due to drug interaction with the hERG potassium channel is measured during the test pulse and is noted as "test current". In cell lines of the invention, the test current varies by less than approximately 20% in a control situation, lasting up to one hour. The term "patch clamp apparatus" refers to any instrument or device suitable for conducting such measurements, such as, for example, standard patch clamp, an IonWorks HT, IonWorks Quattro, PatchXpress 7000A and the like.

"Subject" includes mammals and birds. "Mammals" means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. The term "subject" does not denote a particular age or sex.

"Treating" or "treatment" of a disease state includes (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms; or (iii) relieving the disease state, i.e., causing temporary or permanent regression of the disease state or its clinical symptoms.

All patents and publications identified herein are incorporated herein by reference in their entirety.

General Method

The invention provides cell lines that express hERG and are suitable for use in automated, high throughput electrophysiology assays, and methods for using such cells to screen compounds for potential hERG inhibitory activity.

The cell lines of the invention are designed for use in planar patch electrophysiology systems by virtue of the fact that they are adapted to growth in suspension. They have been used on systems like the IonWorks HT planar patch system and the PatchXpress 7000A, but may be used in other devices or systems as well.

Cell lines can be cultured in suspension using Ex-cell 301 (JRH, Cat JRH-14331), 10% Fetal Bovine Serum (Gibco, Cat 16140-089) and 0.25 mg/ml Geneticin (Gibco, Cat 10131-035). Cells are preferably grown at 35±2 C, supplemented with 5% $CO_2$, in 50-100 ml volumes in 1 liter shake flasks, at 90-100 rpm (2 inch shaker amplitude). For optimal performance, cell titers are kept between about $10^5$ and about $10^6$ cells/ml.

Expression of hERG can be verified by standard methods, for example by Western blot after cell lysis. Expression of hERG current can vary depending on cell culture conditions.

The stability of a cell line can be assessed using a standard patch clamp method, by clamping cells obtained from the cell line, pulsing them, and measuring the resulting currents at a plurality of time points. In a stable cell line of the invention, the current does not vary by more than 20% in one hour under control conditions.

For adherent cells, removal usually requires the use of a dissociation reagent, such as culture medium supplemented with trypsin or Versene™. For suspension adapted cells, no dissociation reagent is typically required. Cells are resuspended in the electrophysiology recording solution prior to experimental use.

HERG current measurements are conducted on the cells of the invention in the presence and absence of test compounds. For screening purposes, it is sufficient to note the concentration at which the test compound inhibits the hERG current by about 50% or greater.

In the practice of the methods of the invention, cells from a cell line of the invention are contacted with or exposed to test compounds, optionally including positive and negative control compounds, and the degree to which hERG activity is inhibited is measured by determining the effect (if any) on current during electrophysiological measurements. Thus, for example, one can apply cells of the invention to a patch clamp apparatus substrate, and contact individual cells with a test compound. The test compounds may be used in a plurality of concentrations, or may all be used at a predetermined concentration (for example, 10 µM, 20 µM, 50 µM, and the like). Compounds are typically dissolved in electrophysiological recording solution. The cells are then patch clamped and pulsed as described herein, and the test current detected. Compounds that cause a substantial decrease in test current are considered to inhibit hERG activity at that concentration. Preferably, the test current is compared against one or more controls, which may be the same cells of the invention prior to application of the test compounds, or may be substantially identical cells (for example, derived from the same cell culture) and subjected to positive and/or negative control compounds.

Utility

The cell lines of the invention are useful for providing cell-surface expression of hERG in stable yield, and serve as suitable substrates for high throughput hERG activity screening using electrophysiological methods. Thus, using the cell lines of the invention, one can screen drug candidates quickly and efficiently for their possible interaction with hERG. Methods of the invention are useful for high throughput screening of drug candidates and other compounds, to determine their interaction and/or modulation of hERG, and thus an element of their potential cardiotoxicity.

EXAMPLES

The following preparations and examples are given to enable those skilled in the art to more clearly understand and to practice the present invention. They should not be considered as limiting the scope of the invention, but merely as being illustrative and representative thereof.

Cell culture media components included Ex-cell 301 (JRH, Cat JRH-14331), 10% Fetal Bovine Serum (Gibco, Cat 16140-089) and 0.25 mg/ml Geneticin (Gibco, Cat 10131-035). Cells are grown at 35±2 C, supplemented with 5% $CO_2$, in 50-100 ml volumes in 1 liter shake flasks, at 90-100 rpm (2 inch shaker amplitude). For optimal performance, cell titers are kept between $10^5$ and $10^6$ cells/ml.

Electrophysiology recording solutions for both standard and automated patch clamp (PatchXpress 7000A) include Internal Buffer (in mM, from Sigma unless otherwise noted): 140 KCl (Cat P-9541), 6 EGTA (Cat E-3889), 5 Hepes (Cat H-3784), 5 $MgCl_2$ (Cat M-1028), 5 ATP-$Na_2$ (Cat A-2383) pH 7.2 with KOH (J.T. Baker, Cat 3143-01); External Buffer (in mM, from Sigma unless otherwise noted): 150 NaCl (Cat S-3014), 10 Hepes (Cat H-3784), 4 KCl (Cat P-9541), 1.2 $CaCl_2$ (Cat C-3306), 1 $MgCl_2$ (Cat M-1028), pH to 7.4 with HCL (J.T. Baker Cat 5619-02). Patch Substrates include PatchPlates™ (Cat 9000-0688) and SealChips™ (1-SealChip16-K) distributed by Molecular Devices Corp.

Electrophysiology: Voltage pulse protocol: holding potential was −80 mV, leak subtraction was calculated from a 100 msec pulse to −40 mV, followed by 1000 msec at 20 mV (prepulse), and 500 msec at −40 mV (test pulse). hERG current was measured as the peak (beginning of the test pulse) at −40 mV after correction with leak current.

$IC_{50}$ Curve Generation and Statistics: Concentration-response curves are fitted in Excel Fit (version 3, ID-BS) with the Four Parameter Logistical Model or Sigmoidal Dose Response Model, Equation 205. Fractional inhibition $(I_{Compound}/I_{Control})=1/(1+[Compound]/IC_{50})^{n_H}$, where I is current, $IC_{50}$ is the concentration of compound required to inhibit current by 50% and $n_H$ is the Hill coefficient.

Example 1

CHO-K1 Cell Line Expressing hERG (A) A CHO-K1 cell line stably expressing high levels of functional hERG channels was generated as follows. First, wild type CHO-K1 cells were transfected with a plasmid encoding a (CMV-promoter-cyan fluorescence protein-IRES-hygromycin resistance marker) cassette. Two nonidentical loxP sites are located on this construct, one between the CMV-promoter and the cyan fluorescence protein ORF, and one at the 3'-end of the hygromycin resistance marker. From random CHO cell transfectants growing in hygromycin, one cell line was selected based on its high levels of cyan fluorescence protein expression. These levels remained stable over multiple generations; genomic DNA blotting verified that a single chromosomal integration event had occurred. A (loxP—hERG-IBES-neomycin resistance marker—loxP) cassette was subsequently recombined into this recipient cell line by CRE recombinase mediated exchange. The correct recombination event in selected CHO cell clones was verified by i) absence of cyan fluorescence, ii) sensitivity to hygromycin and iii) successful genomic DNA PCR using a forward primer located in the CMV promoter and a reverse primer in the hERG-ORF. Transfection and subsequent selection of 5 million cells yielded 16 clones that satisfied the above three criteria. These clones were scaled up and analyzed for expression of hERG protein by western blot and hERG ion channel activity on the Ionworks instrument. One resulting cell line, "CHO crelox hERG UG#7", was subsequently adapted to growth in suspension. An initial suspension culture was prepared by diluting cells to 0.75 million/ml in Ex-cell 301 medium, 5% FBS, 0.25 mg/ml G418. This culture was grown for 24 hrs, and reached a density of about $10^6$ cells/ml. It was then diluted to 0.2 million cells/ml in fresh medium, and grown for 72 hrs, to reach a density of $10^6$ cells/ml. This dilution-transfer was repeated four times, at which point the cells were considered adapted to suspension culture. This cell line was deposited to ATCC under the provisions of the Budapest Treaty under accession number PTA-6812 on Jun. 22, 2005.

Example 2

Evaluation of Cells Expressing hERG

A description of the cell line using the IonWorks HT instrument has been documented: H. Guthrie, et al. (2005). "A Place for High Throughput Electrophysiology in Cardiac Safety: Generating a Novel hERG Cell Line and Screening Early with IonWorks HT." *J Biomol Screening* (2005) 10(8): 832-40.

A description of the cell line using the PatchXpress 7000A instrument has been documented: L. Guo and H. Guthrie (2005). "The Role of Automated Electrophysiology in the Prediction of QT Prolongation." *J Pharmacol Toxicol Methods* 52(1):123-35.

Example 3

High-Throughput Screening of hERG Activity

The cell line CHO crelox hERG UG#7 exhibited an average current amplitude of 800 pA, >80% seal rate success, seals between 100-200 MOhm and greater than 80% overall successful recordings, and was chosen to be used in the compound library screen. Three hundred compounds were screened to find those compounds which inhibited >50% of hERG current after a 30 μM compound application. Compounds from several projects were used for the screen, some of which were already known to block hERG channels when studied by standard patch clamp, although the experiments here were performed blinded. Three compound plates were prepared on 96-well plates and each was run twice, with approximately 90 compounds per plate (each compound was tested four times). Utilizing the 384-well PatchPlate, the 300 compound single-point screen was completed in one eight-hour day. One run using a compound plate took approximately 40 min. In total, each compound was used in eight PatchPlate wells, generally allowing between three and eight successful cells (data points) at the one concentration.

During the screen, each compound concentration was screened twice to ensure a sufficient number of cells per data point. The redundancy of eight wells was necessary because of the variability in success rate. Thus is it possible to have a range in n values from one to eight for each compound. Replicate PatchPlate wells are also important because of cell-to-cell variability within a cell line. FIG. 2 shows variability observed with the CHO crelox hERG UG#7 cell line over nine experimental days (non-consecutive). During this time, after the initial cell line evaluation, this cell line produced an average current amplitude of 650 pA, which was reduced from the 800 pA observed in the cell line evaluation phase of this study. Current stability was high and approached 90%. While replicates used in these experiments may have increased our screening time, sufficient data was produced within the screening time designated. With the new IonWorks Quattro, a technology incorporating Population Patch Clamp™ technology (increased number of recording holes in the PatchPlate well), the redundancy practiced here will be eliminated.

At 30 μM, 160 compounds blocked hERG current >50%. The 160 compounds so identified were re-screened using an eight-point concentration-response with the IonWorks HT system. Five drugs were screened per run, along with positive (haloperidol) and negative (PBS with 0.1% DMSO) controls. The average haloperidol $IC_{50}$ generated with IonWorks HT was 0.74+0.36 μM (from 31 experiments). Historic standard patch clamp data for haloperidol collected at 37 C with a different cell line under different experimental conditions varied from 0.025 to 0.12 μM. The 160 compound screen took five days to complete with an individual concentration tested in 16 PatchPlate wells. As previously discussed, the redundancy in compound testing was to ensure a large number of data points were produced to build confidence in the data set. One data set originating from one project was selected for further evaluation since all compounds in this subset had been tested by standard patch clamp. The historic patch clamp data and IonWorks HT data were positively correlated (Spearman r=0.53, p<0.004). Compounds that yielded a hERG $IC_{50}$ value >30 μM on IonWorks HT had an average standard patch clamp $IC_{50}$ value of 20.2+10.0 μM (SD). The standard patch clamp values were collected under slightly different conditions including whole cell configuration (versus perforated patch), voltage pulse protocol, recording solutions, cell line (CHO-hERG), temperature (37 C), and analysis methods. Some compounds appeared to be less potent with the IonWorks HT system, and a few even slightly more potent. However, the average $IC_{50}$ values of both groups showed no statistical difference.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed:

1. A method for determining the ability of a test compound to inhibit hERG, said method comprising:
    a) providing a stable eukaryotic cell that expresses hERG and exhibits a variation in test current of less than 20% on successive electrophysiological measurements in a patch clamp apparatus under control conditions, wherein said stable eukaryotic cell comprises CHO cre-lox-hERG UG#7 (ATCC PTA-6812);
    b) contacting said cell with a test compound;
    c) measuring a test current in a patch clamp apparatus; and
    d) determining if the test current is reduced in the presence of said test compound.

2. The method of claim 1, wherein said test current in said cell is compared before and after contacting said cell with said test compound.

3. The method of claim 1, wherein said test current in said cell is compared against a test current in a substantially identical cell in the absence of said test compound.

4. The method of claim 1, wherein said test current in said cell is compared against a test current in a substantially identical cell contacted with a compound known to have no hERG-inhibitory effects.

5. The method of claim 1, wherein said test current in said cell is compared against a test current in a substantially identical cell contacted with a compound known to exhibit an unacceptable level of hERG inhibition.

* * * * *